(12) United States Patent
Cuzzato et al.

(10) Patent No.: US 6,348,634 B1
(45) Date of Patent: Feb. 19, 2002

(54) PROCESS FOR THE (CFC-113A) DIMERIZATION

(75) Inventors: Paolo Cuzzato; Ornella Majaron, both of Treviso; Francesco Pinna, Venice, all of (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/496,184

(22) Filed: Feb. 2, 2000

(30) Foreign Application Priority Data

May 2, 1999 (IT) .......................... MI99A0221

(51) Int. Cl.⁷ .............................. C07C 17/02
(52) U.S. Cl. ........................ 570/153; 570/171
(58) Field of Search ................. 570/153, 171

(56) References Cited

U.S. PATENT DOCUMENTS

| | | | |
|---|---|---|---|
| 4,691,067 A | * | 9/1987 | Ng ............................. 570/153 |
| 5,035,564 A | | 7/1991 | Cheminal et al. .......... 570/176 |
| 5,382,720 A | | 1/1995 | Ikawa et al. ................ 570/153 |
| 5,516,951 A | * | 5/1996 | Aoyama ..................... 570/153 |
| 5,536,890 A | | 7/1996 | Bielefeldt et al. .......... 570/175 |

FOREIGN PATENT DOCUMENTS

| | | |
|---|---|---|
| EP | 0 073 055 A1 | 3/1983 |
| EP | 0 879 790 A1 | 11/1998 |
| WO | WO 95/05353 | 2/1995 |

OTHER PUBLICATIONS

Patent Abstracts of Japan (JP 05 201700) (1995).

* cited by examiner

*Primary Examiner*—Alan Siegel
(74) *Attorney, Agent, or Firm*—Arent Fox Kintner Plotkin & Kahn, PLLC

(57) ABSTRACT

A reductive dimerization process of 1,1,1-trifluoro, 2,2,2-trichloroethane (CFC-113a) with hydrogen, with formation of 1,1,1,4,4,4-hexafluoro-2,2,3,3-tetrachlorobutane and 1,1,1,4,4,4-hexafluoro-2,2-dichlorobutene, and mixtures thereof, wherein the catalyst is constituted by metal ruthenium supported on graphitized carbon obtainable by treatment of the carbon at temperatures higher than 2000° C., in inert gas, or aluminum fluoride having an high surface area.

11 Claims, No Drawings

PROCESS FOR THE (CFC-113A) DIMERIZATION

The present invention relates to a process for the reductive dimerization of 1,1,1-trifluoro, 2,2,2-trichloroethane (CFC-113a) with hydrogen, which allows to obtain with improved yields 1,1,1,4,4,4-hexafluoro-2,2,3,3-tetrachlorobutane, from now on called SD (saturated dimer), and 1,1,1,4,4,4-hexa-fluoro-2,3-dichlorobutene, from now on called UD (unsaturated dimer), so mixtures thereof.

Said compounds are used in hydrogenation processes known in the prior art for the 1,1,1,4,4,4-hexafluorobutane (HFC-356) synthesis, which is used to replace the CFCs banned by the Montreal Protocol, since it is not dangerous for the ozone layer.

U.S. Pat. No. 5,382,720 describes the production of intermediates to be subjected to hydrogenation to give HFC-356. These compounds are obtained by dimerization in gaseous phase of 1,1,1 trifluoroethane halogenated derivatives containing from one to three chlorine atoms. By this reaction, by using as catalyst nickel, preferably supported on silicon oxide (silica), one or three chlorine atoms of 1,1,1 trifluoroethane can be replaced by fluorine, as shown in the Examples. The use of a silicon oxide-based catalyst gives some problems from the industrial point of view. In the hydrogenation of fluorinated hydrocarbons partially chlorinated with this support, hydrochloric acid is formed together with hydrofluoric acid traces. These acids attack the support itself forming compounds as silicon chlorides and oxyhalides (and fluorides), which at room temperature are generally liquids and some of them also gaseous. Under these conditions the catalyst is degraded. In said patent an additional step is contemplated to absorb on calcium oxide the hydrohalogenic acids present in the reaction gas.

U.S. Pat. No. 5,536,890 relates to a process for the HFC 356 production by dimerization and then by hydrogenation in gaseous phase, on Pd/Ni catalyst on active carbon support, of an halogenated derivative (halaogen=chlorine, bromine) of trifluoroethane, specifically CFC 113a, and subsequent gaseous hydrogenation under the same conditions. The dimerization reaction yields are very low. See the Examples of the patent.

The need was therefore felt to have available an industrial process to produce, starting from CFC 113a, with improved yields, precursors to obtain HFC-356, by using stable catalysts in the reaction conditions.

It has surprisingly and unexpectedly been found by the Applicant a process wherein the dimerization by hydrogenation in vapour phase of FC 113a takes place with improved yields, in the presence of a catalyst supported on the materials described hereinunder.

It is an object of the present invention a process for the reductive dimerization of 1,1,1-trifluoro, 2,2,2-trichloroethane (CFC-113a) with hydrogen, with formation of 1,1,4,4,4-hexafluoro-2,2,3,3-tetrachlorobutane and 1,1,-1,4,4,4-hexafluoro-2,3-dichlorobutene, and mixtures thereof, on a catalyst constituted by metal ruthenium supported on one of the following materials:
  a) grafted carbon obtainable by treatment of the carbon at temperatures higher than 2000° C., in inert gas, according to known methods in the prior art, having surface area in the range 350–100 m$^2$/g BET, preferably 350–250 m$^2$/g BET, or
  b) aluminum fluoride having an high surface area, not lower than 25 m$^2$/g, preferably not lower than 30 m$^2$/g and a pore volume not lower than 0.20 cc/g, prepared by fluorination with gaseous HF of an alumina containing from 0.5 to 15% by weight of silicon oxide, and having a surface area of at least 150 m$^2$/g with pore volume not lower than 0.3 cc/g.

With aluminum fluoride, according to the present invention, the alumina fluorination product is meant, with a fluorine content not lower than 90% by weight, preferably not lower than 95%, with respect to the stoichiometric.

The aluminum fluoride surface area is preferably not lower than 30 m$^2$/g and the pore volume is not lower than 0.25 cc/g.

The particle sizes of the materials used as catalyst support are not critical. The support can be in the form of pellets, having sizes of some millimeters, or of granules with a diameter in the range of some tenths and some hundreds of micron.

The catalyst is prepared by impregnating the support with an aqueous solution of a soluble ruthenium salt, preferably a trivalent ruthenium salt, by using the method known as "dry impregnation". The impregnated support is dried in stove at 110° C. for some hours, then, preferably, calcined at 400° C. in air flow for 4 hours, reducing at the end the ruthenium cation to metal by treatment with hydrogen at 400° C. for 7–8 hours.

It has been found by the Applicant that in the absence of the calcination step with air the 113a conversion is higher, but it quickly decreases in the time, while the selectivity is lower (see the Examples).

Preferably the trivalent ruthenium salt is ruthenium chloride RuCl$_3$.

Generally the metal reduction treatment is carried out inside the same reactor wherein the 113a dimerization reaction takes place.

The catalyst ruthenium content is in the range 1–10% by weight, preferably 3–5%.

The reaction is carried out by feeding in the reactor 113a in gaseous phase, pure or optionally in admixture with an inert gas, for example helium.

The 113a feeding to the reactor, determined as ratio between the 113a weight and that of the catalyst, is in the range 0.1–10 h$^{-1}$ (WHSV: weight hourly space velocity).

The reaction temperature is in the range 50°–250° C., preferably 100°–200° C. At higher temperatures the conversion increases but the selectivity decreases. At temperatures lower than 50° C. the conversion is insufficient.

Preferably the hydrogen/113a molar ratio is in the range 3–10.

The pressure is not critical and preferably one operates at atmospheric pressure.

During the use carbonaceous residues deposit on the catalyst, which gradually decrease the efficiency thereof. The catalyst can be easily regenerated by oxidation in air flow at 300°–400° C. for 1 h and subsequently treating with hydrogen at 400° C. for 1.5 h.

The preparation of the aluminum fluoride having a high surface area mentioned in b) is described in the European patent application No. 879,790 in the name of the Applicant herein incorporated by reference.

For the fluorination conditions of the alumina containing silica, one generally operates at temperatures in the range of about 250°–450° C., preferably 300°–400° C. One operates at atmospheric pressure, in the presence of an inert gas in the reaction conditions, for example air or nitrogen; the HF partial pressure must be in the range 0.1–0.5 Atm.

Preferably the reaction takes place in a fluidized bed process. It has been found that in this way the optimal control of the reaction temperature is obtained. For applying this reaction technique the alumina to be fluorinated must have a particle size compatible with the use of fluidized beds.

Generally the alumina used according to the present invention contains less than 0.1% by weight of each of the contaminants of $AlF_3$ final product, such as: iron, sulphates, sodium.

When the aluminas are in the hydrated form, before fluorination it is preferable to calcine in air or in nitrogen atmosphere, at temperatures in the range 300°–400° C. This limits the water development during the reaction, undesirable since it favours the equipment corrosion.

The aluminas containing silica are prepared by known methods in the prior art, for example spray-drying of suitable precursors, and they are commercial products, e.g. those of the firm Condea Chemie (Germany).

The physical characterization of the aluminas and of the aluminum fluorides is carried out by using techniques well known to the skilled man in this field:

- the surface area, determined by nitrogen adsorption according to the BET method;
- the pore volume, measured by mercury intrusion at high pressure;
- the crystalline phases by X ray diffraction;
- the constituent analyses are carried out by wet way according to known methods, or by X ray fluorescence by comparison with standards prepared on the same matrix through calibrated additions.

The obtained $AlF_3$ generally consists prevailingly of gamma phase as described in FR 1,383,927.

The support indicated in a) is commercially available, for example TIMREX® produced by the firm TIMCAL of (CH 5643) Sins—Switzerland.

The Examples reported hereinunder have the aim to illustrate, without anyway limiting it, the process object of the present invention.

EXAMPLES

Example 1a
RU/$AlF_3$ Catalyst Preparation 2.0 g of $AlF_3$ having high surface area prepared starting from an alumina containing 1.5% by weight of silica, as described in European patent application EP 879,790, are impregnated with a solution prepared by dissolving 0.217 g of $RuCl_3$ in 1 cc of water; the catalyst is dried in stove at 110° C. for 4 hours, directly calcined in the reactor in air flow at 400° C. for further 4 hours, then reduced in pure hydrogen flow at 400° C. for 7.5 hours. The theoretic Ru content is 5% by weight.

Example 1b
113a Dimerization Reaction by Using the Catalyst Prepared According to Example 1a 0.5 g of catalyst of Example 1 are introduced in a glass tubular reactor, having an internal diameter of about 1.1 cm, wherein 5 scc/min of 113a and 30 scc/min of hydrogen (scc=ml of gas measured at 25° C. and 760 mm Hg) are fed at atmospheric pressure and at the temperatures mentioned below. The gases outflowing from the reactor are let bubble in water to remove HCl and possible HF traces, then analyzed by gas-chromatography. The mixture component percentages are expressed as gaschromatographic peak area %.

Dimerization Test at 130° C.

At 130° C. the 113a conversion, measured after 1 h, is 35%, and it decreases to 32% after 24 hours of catalyst use. The selectivity in useful products (SD+UD), measured after 1 h, is 90% and that in $CHCl_2CF_3$ (HCFC-123) is about 2%. The SD/UD is about 1/10. The selectivities for the various products remain substantially unchanged during 24 hours (90% in SD+UD).

Dimerization Test at 150° C.

At 150° C. the 113a conversion, determined after 1 h, is 52% but the catalyst deactivation is very quick: after 24 hours the conversion is 40%. The selectivity in useful products, determined after 1 h, is 80–85% and that of HCFC 123 is about 5%. The SD/UD ratio is initially very low and progressively increases with the gradual catalyst deactivation and reaches the maximum value of about 1/10. After 24 h the selectivity in useful products is 90%.

From the comparison of the dimerization at 130° and 150° C. it follows that it is preferable to work at 150° C. since the unsaturated product amount is clearly higher.

Example 2a
Preparation of the Graphitized Ru/C Catalyst

The catalyst is prepared in the same way of Example 1a, except that, as support, carbon treated at 2000° C., TIMREX® HSAG300 mark, having a surface area of 280 $m^2$/g BET, produced by TIMCAL of Sins (Switzerland), is used. The nominal content in Ru is equal to 5% by weight.

Example 2b
113a Dimerization Reaction by Using the Catalyst of Example 2a 0.5 g of the catalyst of Example 2a are introduced in a glass tubular reactor, having an internal diameter of about 1.1 cm. 5 scc/min of CFC 113a and 30 scc/min of hydrogen are introduced at atmospheric pressure and at the temperatures mentioned hereinunder. The gases flowing from the reactor are let bubble in water to remove HCl and possible HF traces, then analyzed by gaschromatography.

Dimerization Test at 100° C.

At 100° C. the 113a conversion, measured after 1 h, is 28%, and remains constant for about 48 hours, The selectivity in useful products measured after 1 h, is 90%, of which SD represents 6%; the selectivity in HCFC 123 is of 1%.

Dimerization Test at 130° C.

At 130° C. the 113a conversion, measured after 1 h, is 60%, and it remains constant for 24 hours. The selectivity in useful products measured after 1 h, is 90%. SD is about 1–2% of the useful products. The selectivity in HCFC 123 is 1–2%.

The selectivity in useful products remains constant in the time both at 100° C. and at 130° C.: after 24 h it is 90%.

Example 3a
Preparation of the Graphitized Ru/C Catalyst by Omitting the Calcination Step A catalyst is prepared on the same support and with the same Ru content of Example 2a, except that the air calcination step before the reduction with hydrogen is omitted.

Example 3b
113a Dimerization Reaction by Using the Catalyst of Example 3a 0.5 g of the catalyst of Example 3a are introduced in a glass tubular reactor, having an internal diameter of about 1.1 cm, wherein 5 scc/min of 113a and 30 scc/min of hydrogen are fed at atmospheric pressure and at the temperatures mentioned below. The gases flowing from the reactor are let bubble in water to remove HCl and possible HF traces, then analyzed by gaschromatography.

Dimerization Test at 100° C.

At 100° C. the 113a conversion, determined after 1 h, is 50%, with a selectivity of about 50% in useful products (practically only UD), and of 35% in HCFC 123. After about 20 hours of working the conversion decreases to about 35% and the selectivity in useful products rises to 72%; for HCFC 123 it results 7%.

Example 4a (Comparative)
Ru/C Catalyst Preparation According to the Prior Art

The catalyst is prepared according to the procedure of Example 1 of U.S. Pat. No. 5,053,564, as described hereinafter. 1.9 g of commercial active carbon having surface area of 1000 m$^2$/g and pore volume of 0.6–0.7 cc/g, are impregnated with a solution prepared by dissolving 0.2 g of RuCl$_3$ in 1.3 ml of water. The catalyst is dried, introduced into the reactor and pretreated as described in Example 1a. The nominal Ru content is 5% by weight.

Example 4b (Comparative)
113a Dimerization Reaction by Using the Catalyst of Example 4a 0.5 g of the catalyst of Example 4a are introduced in a glass tubular reactor, having an internal diameter of about 1.1 cm, and 5 scc/min of 113a and 30 scc/min of hydrogen are fed at atmospheric pressure and at the temperatures mentioned below. The gases outflowing from the reactor are let bubble in water to remove HCl (and possible HF traces) and then analyzed by gaschromatography.
Dimerization Test at 105° C.

At 105° C. the conversion is 31% with a selectivity in UD of 21% and of 66% in HCFC-123.
Dimerization Test at 130° C.

At 130° C. the CFC-113a conversion is of 88%, the selectivity in UD is 10% and in HCFC-123 of 85%.

Example 5a (Comparative)
Preparation of the RU Catalyst on AlF$_3$ Support not Prepared According to the Invention 2.0 g of AlF$_3$ prepared in the same way as in Example 1a except that alumina free from silica (Condea Pural) is used, are impregnated with a RuCl$_3$ solution and then activated as described in Example 1a. The nominal Ru content is 5% by weight.

Example 5b (Comparative)
113a Dimerization Reaction by Using the Catalyst of Example 5a 0.5 g of the catalyst of Example 5a are introduced in a glass tubular reactor, having an internal diameter of about 1.1 cm, wherein 5 scc/min of 113a and 30 scc/min of hydrogen are fed at atmospheric pressure and at the temperatures mentioned below. The gases outflowing from the reactor are let bubble in water to remove HCl (and possible HF traces) and then analyzed by gaschromatography.
Dimerization Test at 130° C.

At 130° C. the 113a conversion, determined after 0.5 h, is 43% and decreases to 41% after 2 running hours. The selectivity in useful products (SD+UD) after 0.5 h is 77% and that in HCFC 123 of 5%.

The selectivity slowly decreases during the time. After 2 hours the selectivity in useful products is 75%.

Example 6a
Preparation of the Graphitized Ru/C Catalyst

The catalyst is prepared in the same way as in Example 1a, except that, as support, carbon treated at 2000° C, TIMREX® HSAG100 mark, having 130 m$^2$/g BET surface area, produced by TIMCAL of Sins (Switzerland), is used. The nominal Ru content is equal to 5% by weight.

Example 6b
113a Dimerization Reaction by Using the Catalyst of Example 6a 0.5 g of the catalyst of Example 6a are introduced in a glass tubular reactor, having an internal diameter of about 1.1 cm. 5 scc/min of CFC 113a and 30 scc/min of hydrogen are fed at atmospheric pressure and at the temperatures mentioned below. The gases coming out from the reactor are let bubble in water to remove HCl and possible HF traces, then analyzed by gaschromatography.

At 130° C., after 1 hour, the 113a conversion is 60% and the selectivity in useful products (SD+UD) is 80%.

After 27 hours the conversion is 55% while the selectivity remains unchanged (80%).

TABLE 1

Summary of the results obtained in the Examples

| Ex. | temperature and dimerization time | dimerization products | conv. % | selectivity in the dimerization products % |
|---|---|---|---|---|
| 1b | T = 130° C. t = 1h | SD + UD | 35 | 90 |
|    | T = 130° C. t = 24h | " | 32 | 90 |
|    | T = 150° C. t = 1h | " | 52 | 80–85 |
|    | T = 150° C. t = 24h | " | 24 | 90 |
| 2b | T = 100° C. t = 1h | SD + UD | 28 | 90 |
|    | T = 100° C. t = 48h | " | 28 | 90 |
|    | T = 130° C. t = 1h | " | 60 | 90 |
|    | T = 130° C. t = 24h | " | 60 | 90 |
| 3b | T = 100° C. t = 1h | UD | 50 | 50 |
|    | T = 100° C. t = 20h | " | 35 | 72 |
| 4b comp. | T = 105° C. | UD | 31 | 21 |
|    | T = 130° C. | " | 88 | 10 |
| 5b comp. | T = 130° C. t = 0.5h | SD + UD | 43 | 77 |
|    | T = 130° C. t = 2h | " | 41 | 75 |
| 6b | T = 130° C. t = 1h | SD + UD | 60 | 80 |
|    | T = 130° C. t = 27h |  | 55 | 80 |

What is claimed is:

1. A reductive dimerization process of 1,1,1-trifluoro,2,2,2-trichloroethane (CFC-113a) with hydrogen with formation of 1,1,1,4,4,4-hexafluoro-2,2,3,3-tetrachloro-butane and 1,1,1,4,4,4-hexafluoro-2,3-dichlorobutene, and mixtures thereof, wherein the catalyst is formed of metal ruthenium supported on one of the following materials:
   a) graphitized carbon obtainable by treatment of the carbon at temperatures higher than 2000° C., in inert gas, having surface area in the range 350–100 m$^2$/g BET, or
   b) aluminum fluoride having a high surface area, not lower than 25 m$^2$/g, and a pore volume not lower than 0.20 cc/g, prepared by fluorination with gaseous HF of an alumina containing from 0.5 to 15% by weight of silicon oxide, and having a surface area of at least 150 m$^2$/g with pore volume not lower than 0.3 cc/g.

2. The process according to claim 1 wherein the aluminum fluoride has a fluorine content not lower than 90% by weight, with respect to the stoichiometric.

3. The process according to claim 1 wherein the pore volume of the aluminum fluoride is not lower than 0.25 cc/g.

4. The process according to claim 1 wherein the catalyst ruthenium content is in the range 1–10% by weight.

5. The process according to claim 1 wherein the 113a feeding to the reactor, determined as ratio between the 113a weight and that of the catalyst, is in the range 0.1–10 h$^{-1}$ (WHSV).

6. The process according to claim 1 wherein the reaction temperature is in the range 50°–250° C.

7. The process according to claim 1 wherein the hydrogen/113a molar ratio is in the range 3–10.

8. The process according to claim 1 wherein the catalyst is regenerated by oxidizing in air flow at 300°–400° C. for 1 h and subsequently treating with hydrogen at 400° C. for 1.5 h.

9. The process according to claim 1 wherein the graphitized carbon has a surface area in the range 350–250 m$^2$/g BET.

10. The process according to claim 1 wherein the aluminum fluoride has a high surface area not lower than 30 m$^2$/g.

11. The process according to claim 2 wherein the aluminum fluoride has a fluorine content not lower than 95% by weight, with respect to the stoichiometric.

* * * * *